United States Patent
Van Heumen

(10) Patent No.: US 10,420,197 B2
(45) Date of Patent: Sep. 17, 2019

(54) RADIATION SOURCE, METROLOGY APPARATUS, LITHOGRAPHIC SYSTEM AND DEVICE MANUFACTURING METHOD

(71) Applicant: ASML Netherlands B.V., Veldhoven (NL)

(72) Inventor: Martijn Petrus Christianus Van Heumen, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/888,362

(22) Filed: Feb. 5, 2018

(65) Prior Publication Data

US 2018/0160520 A1   Jun. 7, 2018

Related U.S. Application Data

(62) Division of application No. 15/103,721, filed as application No. PCT/EP2014/074659 on Nov. 14, 2014, now Pat. No. 9,924,585.

(30) Foreign Application Priority Data

Dec. 13, 2013   (EP) .................................... 13197290

(51) Int. Cl.
*G03F 7/20*     (2006.01)
*H05G 2/00*     (2006.01)
(Continued)

(52) U.S. Cl.
CPC ......... *H05G 2/008* (2013.01); *G01N 21/9501* (2013.01); *G03F 7/70191* (2013.01);
(Continued)

(58) Field of Classification Search
CPC .. G03F 7/70033; G03F 7/70016; H01J 65/04; H05G 2/003; H05G 2/008
See application file for complete search history.

(56) References Cited

U.S. PATENT DOCUMENTS

| | | |
|---|---|---|
| 3,590,306 A | 6/1971 | Burnham et al. |
| 4,954,756 A | 9/1990 | Wood et al. |

(Continued)

FOREIGN PATENT DOCUMENTS

| | | |
|---|---|---|
| CA | 902702 | 6/1972 |
| CH | 666 776 A5 | 8/1988 |

(Continued)

OTHER PUBLICATIONS

English-Language Abstract for Swiss Patent Publication No. CH 666776, published Aug. 15, 1988; 2 pages.

(Continued)

*Primary Examiner* — Steven Whitesell Gordon
(74) *Attorney, Agent, or Firm* — Sterne, Kessler, Goldstein & Fox P.L.L.C.

(57) ABSTRACT

A radiation source apparatus comprising: a container for being pressurized with a gaseous medium in which plasma which emits plasma emitted radiation is generated following excitation of the gaseous medium by a driving radiation, wherein said container is operable substantially to remove radiation with a wavelength of 10-400 nm from said plasma emitted radiation before said plasma emitted radiation exits said container as output radiation. In an embodiment the container comprises: an inlet radiation transmitting element operable to transmit said driving radiation from outside said container to inside said container, and an outlet radiation transmitting element operable to transmit at least some of said plasma emitted radiation from inside said container to outside said container as output radiation; wherein at least one of said inlet and outlet radiation transmitting elements comprises a plane parallel plate.

6 Claims, 3 Drawing Sheets

(51) Int. Cl.
*H01J 65/04* (2006.01)
*G01N 21/95* (2006.01)
*H01J 61/54* (2006.01)
*H01J 65/00* (2006.01)
*G01N 21/956* (2006.01)
*H01J 61/35* (2006.01)

(52) U.S. Cl.
CPC .............. *H01J 61/54* (2013.01); *H01J 65/00* (2013.01); *H01J 65/04* (2013.01); *G01N 21/956* (2013.01); *H01J 61/35* (2013.01); *H01J 61/545* (2013.01)

(56) References Cited

U.S. PATENT DOCUMENTS

| | | | |
|---|---|---|---|
| 5,493,184 | A | 2/1996 | Wood et al. |
| 5,614,780 | A | 3/1997 | Suzuki et al. |
| 6,504,903 | B1* | 1/2003 | Kondo ............... B82Y 10/00 378/119 |
| 6,509,697 | B2 | 1/2003 | Ervin et al. |
| 6,559,607 | B1 | 5/2003 | Ervin et al. |
| 6,561,675 | B1 | 5/2003 | Kavanagh |
| 6,894,298 | B2 | 5/2005 | Ahmad et al. |
| 7,141,798 | B2 | 11/2006 | Ito et al. |
| 7,488,962 | B2 | 2/2009 | Korobochko et al. |
| 7,541,604 | B2 | 6/2009 | Goetze et al. |
| 7,619,232 | B2 | 11/2009 | Schmidt et al. |
| 7,786,455 | B2 | 8/2010 | Smith |
| 7,897,947 | B2 | 3/2011 | Vaschenko |
| 7,973,261 | B2 | 7/2011 | Lee et al. |
| 8,358,069 | B2 | 1/2013 | Sumitomo et al. |
| 8,867,020 | B2 | 10/2014 | Smilde et al. |
| 9,411,238 | B2 | 8/2016 | Yakunin et al. |
| 9,924,585 | B2 | 3/2018 | Van Heumen |
| 2003/0147499 | A1* | 8/2003 | Kondo ............... H05G 2/001 378/119 |
| 2006/0066855 | A1 | 3/2006 | Boef et al. |
| 2007/0194683 | A1 | 8/2007 | Serita et al. |
| 2007/0228300 | A1 | 10/2007 | Smith |
| 2009/0127479 | A1 | 5/2009 | Hosokai et al. |
| 2010/0140510 | A1 | 6/2010 | Buescher et al. |
| 2010/0140513 | A1* | 6/2010 | Nagai ............... G03F 7/70033 250/504 R |
| 2011/0027704 | A1 | 2/2011 | Cramer et al. |
| 2011/0204265 | A1 | 8/2011 | Smith et al. |
| 2011/0205529 | A1* | 8/2011 | Gross ............... G01J 3/10 356/51 |
| 2012/0242970 | A1 | 9/2012 | Smilde et al. |
| 2013/0134330 | A1* | 5/2013 | Fujimoto ............... G02B 7/028 250/504 R |
| 2013/0181595 | A1 | 7/2013 | Bezel et al. |
| 2013/0329204 | A1 | 12/2013 | Pellemans et al. |
| 2016/0316550 | A1 | 10/2016 | Van Heumen |

FOREIGN PATENT DOCUMENTS

| | | |
|---|---|---|
| DE | 4241911 A1 | 6/1993 |
| DE | 102011113681 A1 | 3/2013 |
| EP | 2175474 A2 | 4/2010 |
| EP | 2312615 A2 | 4/2011 |
| FR | 2554302 | 5/1985 |
| JP | 3048836 | 6/2000 |
| JP | 2003229298 | 8/2003 |
| JP | 2010205577 | 9/2010 |
| KR | 2006/0128510 | 12/2006 |
| KR | 1020110040678 | 4/2011 |
| KR | 1020130135393 | 12/2013 |
| TW | 2009/13797 A | 3/2009 |
| TW | 2009/19525 A | 5/2009 |
| TW | 2013/33542 A | 8/2013 |
| WO | WO 94/08439 A1 | 4/1994 |
| WO | WO 2009/078708 A1 | 6/2009 |
| WO | WO 2009/106279 A1 | 9/2009 |
| WO | WO 2014/000998 A1 | 1/2014 |

OTHER PUBLICATIONS

English-Language Abstract for German Patent Publication No. DE 4241911, published Jun. 17, 1993; 2 pages.
English-Language Abstract for German Patent Publication No. DE 102011113681, published Mar. 21, 2015; 1 page.
English-Language Abstract for Japanese Patent Publication No. JP 3048836, published Jun. 5, 2000; 2 pages.
English-Language Abstract for Korean Patent Publication No. KR 2006 0128510, published Dec. 14, 2006; 1 page.
Schreiber et al., "Radiation resistance of quartz glass for VUV discharge lamps," Institute of Physics Publishing LTD, Journal of Physics D: Applied Physics, vol. 38, No. 17, Aug. 19, 2005; pp. 3242-3250.
Hoppe et al., "Near-edge optical absorption behavior of sputter deposited hafnium dioxide," Journal of Applied Physics, vol. 101, No. 12, Jun. 29, 2007; pp. 123534-1-123534-5.
International Search Report and Written Opinion of the International Search Authority directed to related International Patent Application No. PCT/EP2014/074659, dated Mar. 16, 2015; 26 pages.
International Preliminary Report on Patentability directed to related International Patent Application No. PCT/EP2014/074659, dated Jun. 14, 2016; 19 pages.
English-Language Abstract for French Patent Publication No. FR 2554302, published May 3, 1985; 2 pages.
English-Language Abstract for Japanese Patent Publication No. JP 2003229298, published Aug. 15, 2003; 2 pages.
English-Language Abstract for Japanese Patent Publication No. JP 2010205577, published Sep. 16, 2010; 2 pages.
English-Language Abstract for Korean Patent Publication No. KR 1020110040678, published Apr. 20, 2011; 2 pages.
English-Language Abstract for Korean Patent Publication No. KR 1020130135393, published Dec. 10, 2013; 2 pages.

* cited by examiner

RADIATION SOURCE, METROLOGY APPARATUS, LITHOGRAPHIC SYSTEM AND DEVICE MANUFACTURING METHOD

This application incorporates by reference in their entireties U.S. application Ser. No. 15/103,721, 371(c) Date Jun. 10, 2016, International Application No. PCT/EP2014/074659, filed Nov. 14, 2014 and EP application 13197290, filed Dec. 13, 2013.

BACKGROUND

Field of the Invention

The present invention relates to plasma based radiation sources (photon sources). Such sources may be used for example to provide high brightness illumination in methods and for metrology usable, for example, in the manufacture of devices by lithographic techniques and to methods of manufacturing devices using lithographic techniques.

Background Art

Radiation sources according to the invention may find application in a wide range of situations. As an example application, the following will describe use of the invention as a light source in metrology. As a particular field of application of metrology, the following shall refer for the sake of example to metrology in the manufacture of devices by lithography.

The terms 'light' and 'light source' may be used conveniently to refer to the generated radiation and the radiation (or photon) source itself, without implying any limitation to radiation of visible wavelengths.

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation. From these measured properties a property of interest of the target can be determined. Examples of scatterometers and techniques can be found in patent applications US 2006/066855 A1, WO 2009/078708, WO 2009/106279, and US 2011/0027704 A.

In one commercially available metrology apparatus, the light source is a xenon (Xe) arc-discharge lamp. Light from this lamp is imaged onto the measurement target through an illumination branch of the apparatus sensor, the last stage of which consists of a high-NA objective. The measurement spot may have a diameter of 25 µm, for example. The time required for each measurement depends in practice on the brightness of the light source at a given wavelength or wave range. Future generations of apparatus are desired to provide an increased spectral bandwidth and sensor design with lower transmittance, while keeping the measurement time the same or shorter. Significant source brightness improvements are necessary to fulfill these requirements.

Plasma-based radiation (photon) sources, for example laser driven light sources (LDLS) offer higher brightnesses. Plasmas are generated in a gaseous medium by the application of energy through electric discharge, and laser energy. The spectral distribution of the radiation may be broadband or narrowband in nature, and wavelengths may be in the near infrared, visible and/or ultraviolet (UV) bands. Published patent application US 2011/204265 A1 discloses plasma based light sources including laser driven light sources directed at producing output radiation (at least partly) in the UV band. One of the difficulties with LDLS is the short lifetime of the xenon arc-discharge bulbs used.

SUMMARY OF THE INVENTION

In a first aspect of the invention there is provided a radiation source apparatus comprising: a container for being pressurised with a gaseous medium in which plasma which emits plasma emitted radiation is generated following excitation of the gaseous medium by a driving radiation, wherein said container is operable substantially to remove radiation with a wavelength of 10-400 nm from said plasma emitted radiation before said plasma emitted radiation exits said container as output radiation.

In a second aspect of the invention there is provided a radiation source apparatus comprising: a container for being pressurised with a gaseous medium in which plasma which emits plasma emitted radiation is generated following excitation of the gaseous medium by a driving radiation, said container comprising: an inlet radiation transmitting element operable to transmit said driving radiation from outside said container to inside said container, and an outlet radiation transmitting element operable to transmit at least some of said plasma emitted radiation from inside said container to outside said container as output radiation; wherein at least one of said inlet and outlet radiation transmitting elements comprises a plane parallel plate.

In a third aspect of the invention there is provided a radiation source comprising: a container for being pressurised with a gaseous medium in which plasma which emits plasma emitted radiation is generated following excitation of the gaseous medium by a driving radiation, said container comprising: an inlet radiation transmitting element operable to transmit said driving radiation from outside said container to inside said container, and an outlet radiation transmitting element operable to transmit at least some of said plasma emitted radiation from inside said container to outside said container as output radiation;

wherein the center of the plasma is substantially further from said outlet radiation transmitting element and/or said inlet radiation transmitting element as from the nearest wall of the container.

The radiation source may be applied in metrology, for example in lithography. The invention in another aspect provides method of measuring a property of structures that have been formed by a lithographic process on a substrate, the method comprising the steps of:

(a) illuminating said structures using output radiation of a radiation source apparatus according to the first, second or third aspects of the invention, set forth above;
(b) detecting radiation diffracted by the structures; and
(c) determining from properties of said diffracted radiation one or more properties of the structure.

The invention yet further provides an inspection apparatus for measuring a property of a structure on a substrate, the apparatus comprising: a support for the substrate having said structure thereon; an optical system for illuminating the structure under predetermined illumination conditions and for detecting predetermined portions of radiation diffracted by the component target structures under said illumination conditions; a processor arranged to process information characterizing the detected radiation to obtain a measurement of said property of the structure, wherein said optical system includes a radiation source apparatus according to the invention as set forth above.

The invention yet further provides a lithographic system comprising: a lithographic apparatus comprising: an illumination optical system arranged to illuminate a pattern; a projection optical system arranged to project an image of the pattern onto a substrate; and an inspection apparatus according to an embodiment of the invention as set forth above, wherein the lithographic apparatus is arranged to use the measurement results from the inspection apparatus in applying the pattern to further substrates.

The invention yet further provides a method of manufacturing devices wherein a device pattern is applied to a series of substrates using a lithographic process, the method including inspecting at least one composite target structure formed as part of or beside said device pattern on at least one of said substrates using the aforementioned method of measuring a property of structures that have been formed by a lithographic process on a substrate, and controlling the lithographic process for later substrates in accordance with the result of the inspection method.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying drawings in which.

DETAILED DESCRIPTION OF EXEMPLARY EMBODIMENT

Before describing embodiment of the invention in detail, it is instructive to present an example environment in which embodiments of the present invention may be implemented.

Figure 1:
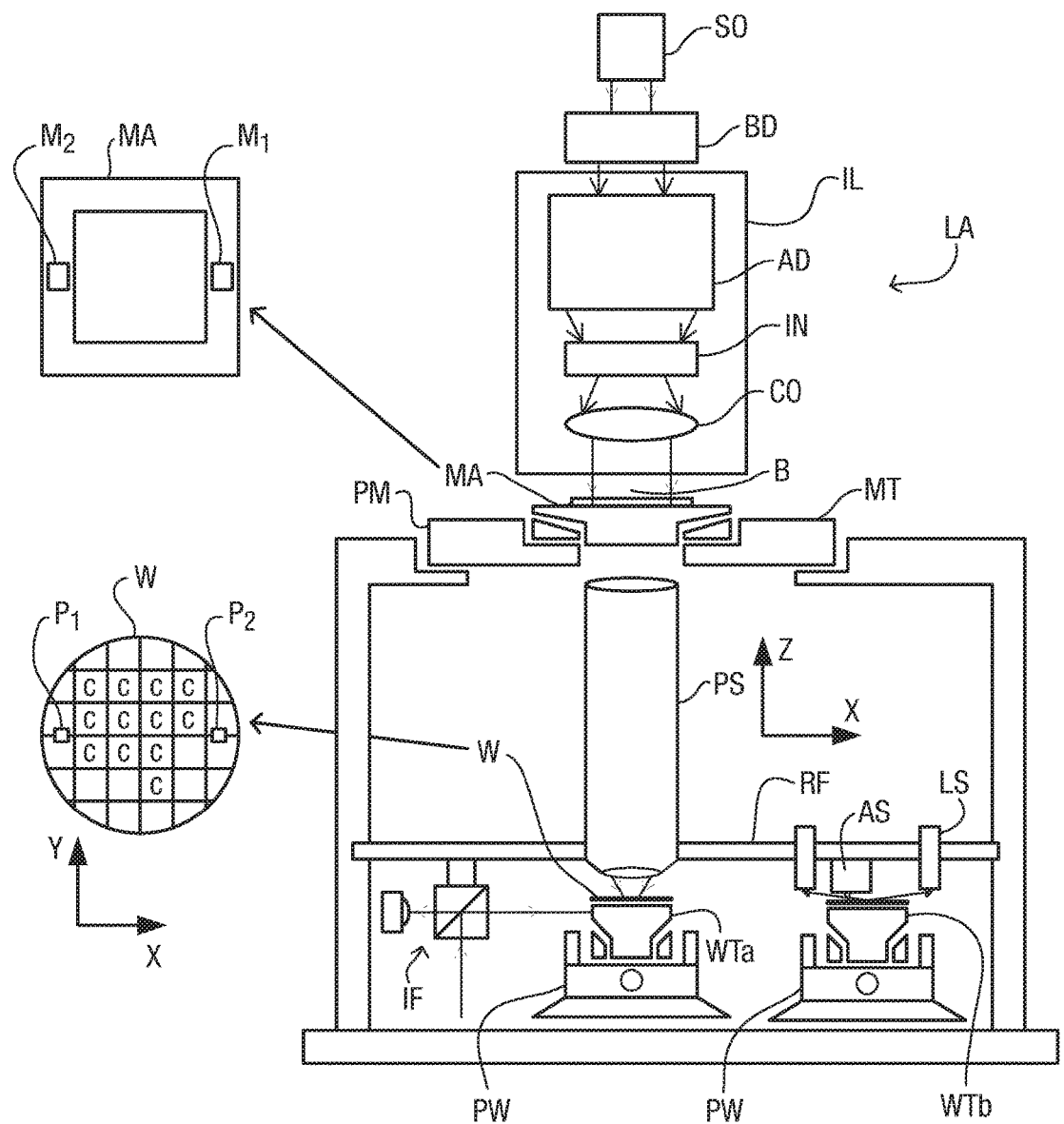
FIG. 1 depicts a lithographic apparatus according to an embodiment of the invention.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan. In general, movement of the patterning device support (e.g., mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g., mask table) MT may be connected to a short-stroke actuator only, or may be fixed.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. The alignment system, which detects the alignment markers, is described further below.

The depicted apparatus could be used in at least one of the following modes:

1. In step mode, the patterning device support (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WT are scanned synchronously while a pattern imparted to the radiation beam is projected onto a target portion C (i.e., a single dynamic exposure). The velocity and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has two substrate tables WTa, WTb and two stations—an exposure station and a measurement station—between which the substrate tables can be exchanged. While one substrate on one substrate table is being exposed at the exposure station, another substrate can be loaded onto the other substrate table at the measurement station and various preparatory steps carried out. The preparatory steps may include mapping the surface level of the substrate using a level sensor LS and measuring the position of alignment markers on the substrate using an alignment sensor AS. This enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations.

Figure 2:
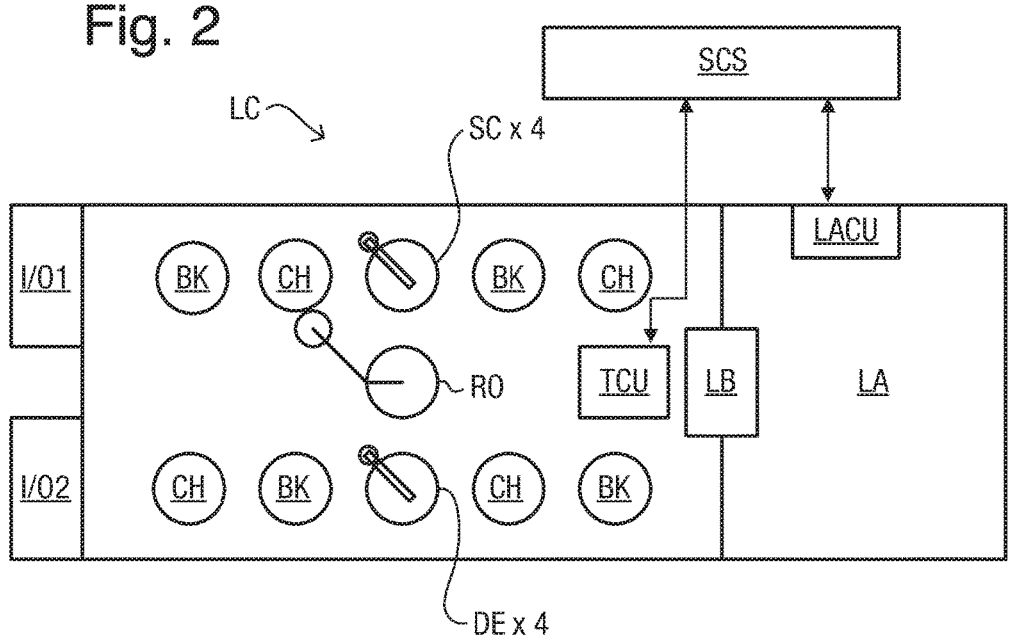
FIG. 2 depicts a lithographic cell or cluster according to an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

Figure 3:
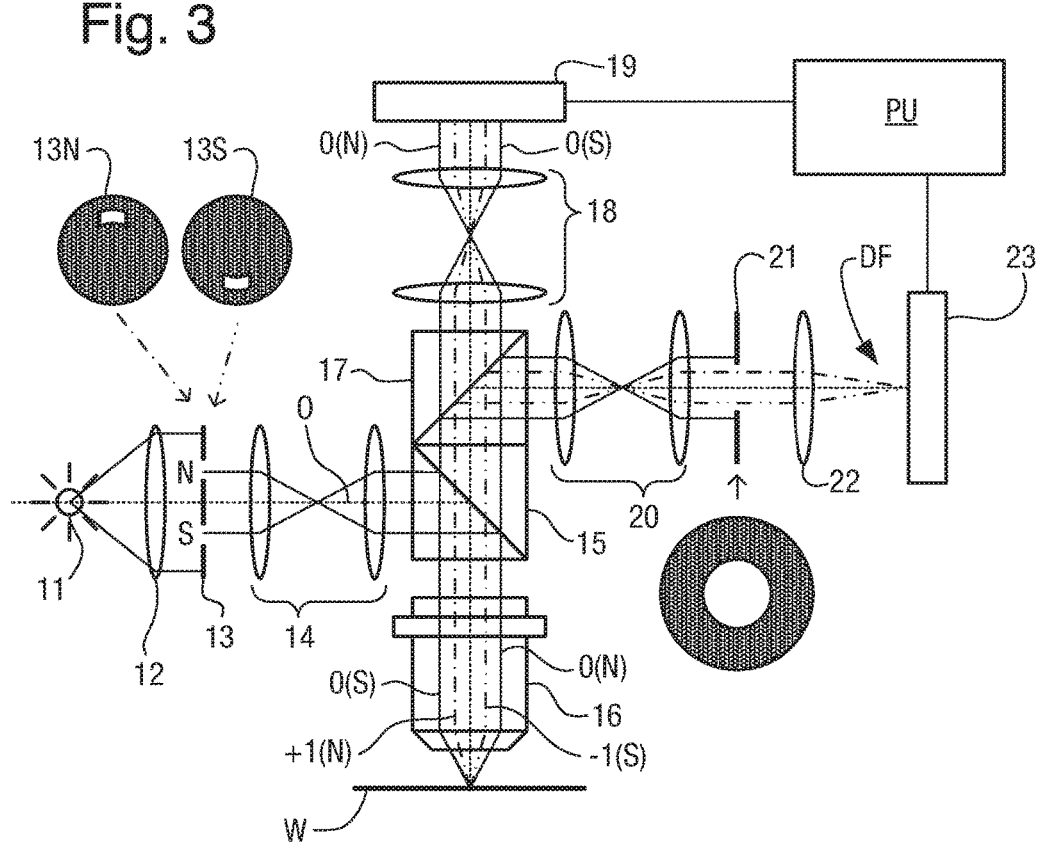
FIG. 3 comprises a schematic diagram of an optical apparatus incorporating a photon source, the apparatus in this example having the form of a scatterometer used in metrology.

FIG. 3 is a schematic diagram of an optical apparatus in the form of a scatterometer suitable for performing metrology in conjunction with the lithocell of FIG. 2. The apparatus may be used for measuring critical dimensions of features formed by lithography, measuring overlay between layers and the like. A product feature or dedicated metrology target is formed on substrate W. The apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 is directed onto substrate W via a beam splitter 15 by an optical system comprising lenses 12, 14 and objective lens 16. These lenses are arranged in a double sequence of a 4F arrangement. A different lens arrangement can be used, provided that it still provides an image of the source on the substrate, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. For example, as illustrated, aperture plate 13 can have different forms, two of which are labeled 13N and 13S, allowing different illumination modes to be selected. The illumination system in the illustrated example forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

At least the 0th and one of the −1 and +1 orders diffracted by the target on substrate W are collected by objective lens 16 and directed back through beam splitter 15. A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can be used for many measurement purposes such as reconstruction.

In the second measurement branch, optical system 20, 22 forms an image of the target on the substrate W on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The image detected by sensor 23 is thus referred to as a 'dark-field' image. Note that the term 'image' is used here in a broad sense. An image of the grating lines as such will not be formed, if only one of the −1 and +1 orders is present.

The images captured by sensors 19 and 23 are output to image processor and controller PU, the function of which will depend on the particular type of measurements being performed. More detail of the apparatus and its applications can be found in the prior patent applications mentioned in the introduction above. The present disclosure is concerned with the construction and operation of the light source 11, to provide higher brightness than the Xe arc lamp used in the known apparatus.

Figure 4:
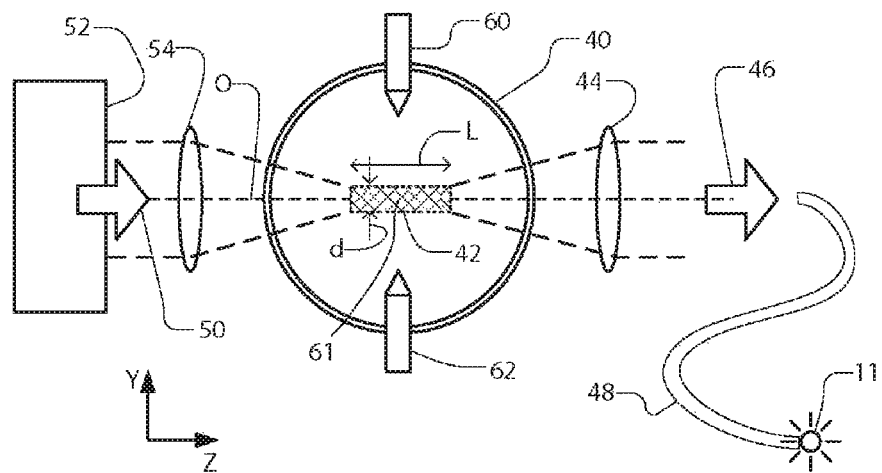
FIG. 4 is a schematic diagram of a radiation source used in the apparatus of FIG. 3.

FIG. 4 shows schematically the principal components of a laser-driven photon source apparatus i.e. a radiation source. The central component is a bulb 40, for example a glass capsule, containing a predetermined gaseous atmosphere. The bulb 40 is an arc bulb designed for exciting gas in the bulb by ionizing it with an electrical field. A suitable gas for example may be xenon (Xe), or a xenon-argon mix. Within this atmosphere, a plasma 42 is generated in a manner to be described, and the plasma emits light (more generally photons of radiation of the desired wavelengths). Collection optics 44 form at least one beam of radiation 46 that may be coupled to a optical fiber 48. Fiber 48 delivers the radiation to the point where it is needed.

When the photon source is used as the source in the apparatus of FIG. 3, the end of fiber 48 forms the source 11 seen in FIG. 3. Collection optics 44 is shown here as a simple lens, but can of course be more complex in a practical embodiment. Reflective rather than refractive optics may be used.

Plasma 42 in this embodiment is generated by application of drive radiation 50 which is generated in this example by a laser 52. Drive optics 54 focus the laser which reaches its narrowest point at the location where the plasma 42 is desired to be formed and maintained.

The laser 52 may be one of a number of different types of high power laser available today or in future. It may for example be a Nd:YAG laser, a CO2 laser, a diode laser, a fiber laser. Drive optics 54 is shown here as a simple lens, but can of course be more complex in practical embodiment. Reflective rather than refractive optics may be used. Further components may be provided to condition the laser radiation in its profile or spectral characteristics. A beam expander may be used, for example.

The laser radiation may be for example in infrared wavelengths, such as 700 to 2000 nm. The plasma 42 will typically be generating radiation at shorter wavelengths in the infrared, visible and/or ultraviolet bands, for example down to 200 nm or below. Among this plasma radiation are the desired wavelengths for use in the metrology apparatus or other application.

Laser energy 50, although very narrowly focused, is not necessarily sufficient to ignite the plasma 42 from a cold start. Therefore, electrodes 60 and 62 are provided with appropriate power and control circuitry (not shown), in order to ignite the plasma 42. These electrodes may be similar to those used in a conventional gas discharge lamp, but are used only during a start-up phase of operation.

In the diagram, axes X, Y and Z are defined for the sake of this description. The Z axis is aligned with an optical axis O. The Y direction is aligned with the electrodes 60, 62. The X axis is transverse to the electrodes, and normal to the plane of the diagram. The apparatus can be constructed or mounted with these axes in any orientation that is convenient for its application. Note that there is no component obstructing the optical path from the plasma 42 to the collection optics 44 in the Z direction other than the radiation transparent material of the bulb 40. There is also in this example nothing obstructing the path of light in the X direction (not shown in this view).

It will be noted that plasma 42, or at least the region of the plasma from which the desired radiation is taken, may be elongate in form, having approximately the shape of a cylinder, or cigar. We will refer to the shape as cylindrical for the sake of explanation. The length of the cylinder is L and its diameter is d. The real plasma will comprise a cloud of elongate form, centered on this cylindrical region. Collection optics 44 is arranged with its optical axis O aligned with the longitudinal direction of the plasma, that is the Z direction in this example. The area of the plasma 42 thus appears as $\pi d^2/4$, that is the area of one end of the cylinder. When L is made substantially greater than d, the depth of plasma from which photons can enter the collection optics through this small area is greater, compared with looking at the plasma in a transverse direction. This allows a higher brightness to be seen over that area, for a given size and intensity of plasma. The etendue of an optical source (or receiver) is broadly speaking the product of the area of the source (receiver) and its exit (entrance) angle. The etendue of the collection optics 44, as with any imaging system, is the product of spot size times the square of its numerical aperture (NA2). The NA in turn is determined by the entrance angle. The etendue of the radiating plasma is in general going to be larger than the etendue of the collection optics 44. Collection optics 44 may be focused at a hypothetical source point 61 midway along the cylinder, as illustrated. In practical examples, the length L of light emitting plasma region 42 may be on the order of a millimeter, say 0.5 to 5 mm. The diameter d may be much smaller, in the range of say 0.01 to 2 mm, for example 0.1 to 1 mm.

In practice, the plasma 42 absorbs very little of the wanted radiation, so that photons emitted anywhere along the length L of the cylinder can travel in the entrance cone of collection optics 44 and into fiber 48. Therefore, compared with the transverse direction, the plasma appears brighter (greater luminous flux per unit area per unit solid angle) than when viewed in the transverse direction. Whereas some laser driven light sources, such as described in US 2011/204265 A1, seek to capture light emitted in the transverse direction, the photon source illustrated herein captures light emitted in the longitudinal direction to exploit the enhanced brightness and smaller extent of the plasma. Either capturing arrangement can be used in combination with the novel concepts disclosed herein.

A difficulty with the radiation source of FIG. 4 is that the bulb 40 is usually in the form of a xenon (Xe) arc-discharge lamp whose design is not optimized for the present use. Normally such a xenon arc-discharge lamp, which consists of a bulb made of glass in which pressurized xenon is placed, is used in a mode in which plasma is created by making an electric arc between the two electrodes 60, 62. However, when the bulb 42 is being used in a laser-driven photon source apparatus such as illustrated in FIG. 4 the bulb 42 tends to suffer from failures. This is thought to be due to thermal stresses set up in the glass and solarization of the glass due to UV radiation. Another difficulty is that the glass of the bulb 40 results in astigmatism; the glass of the bulb 40 is curved and so it behaves as a lens. Due to manufacturing tolerances, the glass of the bulb 40 is never perfectly as designed, so that astigmatism cannot reliably be accounted for in the optical system 44 downstream of the bulb 40.

Figure 5:
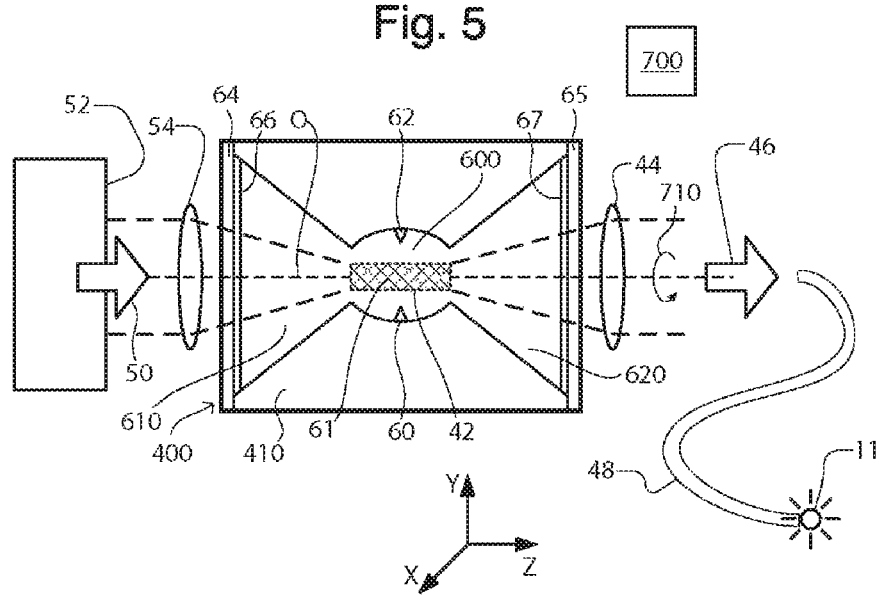
FIG. 5 is a schematic diagram of a radiation source apparatus, according to an embodiment of the present invention.

FIG. 5 shows a radiation source apparatus according to an embodiment of the invention. Note that plasma generation/excitation and collection/transport of the subsequent radiation follow the same structure and process as previously described in relation to FIG. 4.

FIG. 5 shows a container 400 of the present invention which replaces the bulb 40 of FIG. 4. The container 400 contains pressurized xenon (for example between 10 and 30 bar when cold and perhaps between 50 and 100 bar when hot).

The container 400 is an airtight (hermetically sealed) container. In an embodiment the container 400 also comprises at least one radiation transmitting element, e.g. inlet radiation transmitting window 64 and/or outlet radiation transmitting element 65.

In an embodiment, the container 400 comprises at least one filter component, e.g. filter components 66, 67. It should be appreciated that the radiation source does not necessarily have to take the form of that depicted and may take any other suitable form.

Drive radiation 50 may be focused by focusing optics 54 onto plasma 42, entering the container 400 via inlet radiation transmitting element 64. Radiation generated by plasma 42 may exit the container 400 via outlet radiation transmitting element 65, to be collected by collection optics 44.

In an embodiment filter components 66 block ultraviolet radiation (10-400 nm wavelength radiation) exiting the container 400 through inlet radiation transmitting element 64. In an embodiment filter components 67 may block ultraviolet and/or infrared (700-1000 nm wavelength) radiation exiting the container 400 through outlet radiation transmitting element 65.

The filter components 66, 67 may be in the form of a coating. The coating may be on the side of the radiation transmitting element 64, 65 facing the plasma 42 or on the opposite side to the plasma 42. An advantage of the filter component 66, 67 being on the side of the plasma 42 is that the filter component 66, 67 thereby protects the radiation transmitting element 64, 65 from the radiation which is filtered out. If UV radiation is filtered out, this can protect the radiation transmitting element 64, 65 from solarization if the element is susceptible to solarization by UV radiation.

Filter components 66, 67 may be provided in the optical path and made of suitable materials with variable thickness, fixed by the required wavelengths. Filter components 66, 67 may also be integrated with other components of the collection optics 44.

In an embodiment, the filter components 66, 67 and radiation transmitting elements 64, 65 may be incorporated in a single component. For example, the radiation transmitting element 64, 65 may be comprised of a material which absorbs radiation in the desired wavelength range. For example, in order to absorb radiation with a wavelength of 10-400 nm (UV radiation), a radiation transmitting element comprising $TiO_2$ (e.g. glass or other material transparent to radiation coated with $TiO_2$ or glass or other material transparent to radiation doped with $TiO_2$) may be used.

In the case that UV radiation is desired in the beam of radiation 46, the output radiation transmitting element 65 may be comprised of suprasil (®), a synthetic fused silica available from Heraeus Quartzglass, Hanau, Germany.

Radiation transmitting elements 64 and 65 should be gastight and made of suitable coated/uncoated materials. The radiation transmitting elements 64, 65 may also be any size, shape or thickness and/or may be flat/curved. In an embodiment at least one of the radiation transmitting elements 64, 65 comprises a plane parallel plate. This is advantageous as the problem of astigmatism with a bulb 40 such as in FIG. 4 is solved.

In an embodiment the container 400 is made of a size and/or shape such that, in use, the distance between the center 61 of the plasma 42 and the radiation transmitting windows 65, 66 is much larger than that of bulb 40. This is advantageous because any thermal stresses set up on the radiation transmitting windows 64, 65 will be much lower than those in the bulb 40 and the lifetime of the container 400 will therefore be much greater than that of bulb 40. In an embodiment, the center 61 of the plasma 42 is directly between and equidistant from the tips of the electrodes 60, 62 and/or at the focus point of the drive optics 54.

Prior art containers in the form of a bulb 40 are substantially spherical in shape. Therefore, the distance of walls of the bulb (equivalent to the light transmitting windows 65, 66) to the center 61 of the plasma 42 is about equal to the radius of the sphere of the bulb 40. Therefore, in prior art bulbs the distance from the center 61 of the plasma 42 to the light transmitting window 65, 66 is about $$\sqrt[3]{V\frac{3}{4\pi}}$$

where V is the volume of the bulb 42. The inventors have appreciated that the lifetime of the bulb can be significantly increased by using an arrangement in which the center 61 of the plasma 42 is positioned further from the walls on which the plasma emitted radiation impinges which are sensitive to plasma emitted radiation. In an embodiment this is achieved by having a non-spherically shaped container (e.g. an elongate container) in which side walls, at least in a central portion, are comprised of a material more able to withstand plasma emitted radiation impinging on them than the radiation transmitting elements 64, 65.

As illustrated in FIG. 5, the container 400 may contain a volume of gas which extends in the longitudinal direction with the optical axis O. There is a central plasma surrounding volume 600 and on one side a inlet volume 610 and the other side an outlet volume 620. In use, the plasma 42 is in the plasma surrounding volume 600. The driving radiation 50 passes through the inlet volume 610. The plasma emitted radiation passes through the outlet volume 620.

The plasma surrounding volume 600 substantially surrounds the plasma 42 except for radiation and inlet and outlet openings 601, 602 and is for containing gas surrounding the plasma 42.

In an embodiment, the size of the plasma surrounding volume 600 is similar to that of prior art bulb volumes. In an embodiment, the volume of the plasma surrounding volume 600 is less than 200000 $mm^3$ preferably less than 100000 $mm^3$ or even less than 1000 $mm^3$ or even less than 100 $mm^3$. This has the advantage of being quite a small volume so that the plasma 42 is stable and the gas surrounding the plasma 42 does not cool the plasma 42 too much as might occur if the plasma surrounding volume were larger.

In an embodiment, an average cross sectional area in a plane perpendicular to the axis O of the plasma surrounding volume 600 is smaller than the average cross sectional area of the inlet volume 610 and/or outlet volume 620. This arrangement ensures that even for a container 400 with a relatively large volume of gas compared to the prior art, the plasma 42 is stable (because the amount of gas surrounding the plasma 42 is relatively small compared to the overall volume) while still allowing an increase in the distance D relative to a totally spherical volume of container and allowing the collection of a large amount of plasma emitted radiation.

In an embodiment the center 61 of the plasma 42 is substantially further from the outlet radiation transmitting element 66 and/or inlet radiation transmitting element 65 as from the nearest wall of the container 400. In an embodiment, the center 61 of the plasma 42 is at least three times (preferably at least six times) as far from the outlet radiation transmitting element 66 and/or inlet radiation transmitting element 65 as from the nearest wall of the container 400. Thus, in an embodiment, the walls of the container 400 defining the plasma surrounding volume 600 (which are nearest the center 61 of the plasma 42 and do not include the electrodes 60, 62) define a much smaller volume than the total volume of the container 400. This means that the plasma 42 is stable whilst the inlet and outlet radiation transmitting elements 65, 66 are protected from intense plasma emitted radiation.

In an embodiment at least one of a distance between a center 61 of the plasma 42 and said inlet radiation transmitting element 65 and a distance between the center of the plasma and said outlet radiation transmitting element 66 is at least 3 times $$\sqrt[3]{V\frac{3}{4\pi}}$$

wherein V is the volume of the plasma surrounding volume 600. In a preferred embodiment at least one of a distance between a center of the plasma and said inlet radiation transmitting element and a distance between the center of the plasma and said outlet radiation transmitting element at least 6 times $$\sqrt[3]{V\frac{3}{4\pi}}.$$

In an embodiment the plasma 42 is formed at a location at least 10 mm from one or both of the inlet and outlet radiation transmitting elements 64, 65. In a preferred embodiment, at least one of the inlet and outlet radiation transmitting elements 64, 65 is positioned at least 20 mm, more desirably at least 30 mm from the plasma 42 or even more than 35, 40 or 50 mm.

The container 400 comprises an axis of symmetry O extending in the z direction. The plasma 42 is formed on the axis of symmetry O. The inlet and outlet radiation transmitting elements 64, 65 are positioned perpendicular to the axis of symmetry O, which defines a longitudinal direction. Driving radiation 50 travels substantially parallel to the longitudinal axis O. Radiation emitted by the plasma 42 exits through the outlet radiation transmitting element 65 and is substantially parallel to the axis of symmetry O.

In an embodiment the drive optics 54 and/or collection optics 44 are at least partly formed by the inlet radiation transmitting element 64 and outlet radiation transmitting element 65 respectively. That is, one or both the radiation transmitting elements 64, 65 may not be in the form of a plane parallel plate. However, ensuring that the radiation transmitting elements 64, 65 are plane parallel plates makes manufacture of the container 400 less problematic.

The container 400 comprises at least two electrodes 60, 62. The electrodes 60, 62 are provided on either side of the axis O. A body 410 of the container 400 is illustrated as being comprised of a solid material. This is not necessarily the case. However, this may be advantageous for strength and/or heat transfer considerations. Preferably the body 410 (particularly the walls defining the plasma surrounding volume 600, e.g. the central portion of the container 400 walls) is made of a material more able than the radiation transmitting elements 64, 65 to withstand irradiation by plasma emitted radiation. The internal surface of the body 410 of the container 400 may be made of a reflective material. This can aid in maintaining the temperature of the plasma 42 by reflection of radiation emitted by the plasma 42 back to the plasma 42.

In an embodiment, the container 400 may have an internal volume substantially in the shape of two truncated cones orientated with rotational symmetry around the longitudinal axis O with their ends of lower diameter facing each other. A central portion between the two truncated cones may be cylindrical, spherical, ovoid etc. and designed to hold the plasma 42.

The walls of airtight container 400 may be made of suitable materials which are able to block unwanted radiation (or all radiation), for example, materials which block UV radiation generated by the plasma 42. Furthermore, container 400 may be of any dimension, shape and wall thickness to meet the application requirements.

In an embodiment, because the container 400 is airtight and ultraviolet light is filtered out from the output radiation 44 (example.e. at radiation transmitting element 64, 65), ozone produced by ultraviolet light acting on air advantageously does not occur.

It is common for design measures to be taken to try and reduce the length L of the plasma to concentrate its power in a smaller length, the constraints on the plasma shape in the source are relatively relaxed. Whereas, in some prior examples in, the plasma extends longitudinally in what is depicted as the Y direction, between the igniting electrodes, in the illustrated source the plasma in normal operation is arranged so that rays in the longitudinal direction are not obscured, and can be captured by the collection optics 44. Similarly, while in other prior examples the plasma extends in what is depicted as the Z direction, this is obscured by the driving laser optics, and the usable light is captured by a curved mirror, after being emitted in the X and Y directions from the plasma. Thus many prior examples rely on capturing the photons emitted transversely from the plasma. Embodiments of the invention may also or alternatively rely on capturing the photons emitted transversely from the plasma.

It should be noted that the intensity profile of the radiation emitted by the plasma source might not be perfectly uniform across the field of view of collection optics 44. While constraints on the plasma dimensions are relaxed as described above, still the entrance NA of collection optics 44 should be reasonably uniformly filled with radiation. The larger the aspect ratio L/d of the plasma, the smaller the etendue will be in which the radiation is uniformly distributed. Mixing of the light to make it more homogeneous may be desired, for example when the radiation source apparatus is used to deliver a homogeneous light field across aperture 13 in the apparatus of FIG. 3. Sufficient mixing may occur naturally within the fiber 48, or additional measures may be taken. Also, optical properties of the inlet and outlet radiation transmitting elements 64, 65 should be good enough at the key locations that they do not degrade the quality of the drive laser beam or the rays emanating from plasma 42 to collection optics 44. The optical properties of the inlet and outlet radiation transmitting elements 64, 65 and filters 66, 67, should of course be taken into account in designing and setting up the collection optics 44 and focusing optics 54. Functional elements of collection optics 44 and focusing optics 54 can be placed inside container 400 if desired, and/or may be integrated with the wall of the container 400.

In an embodiment the container 400 is substantially rotationally symmetric around the longitudinal axis O. A rotator 700 may be provided to rotate the container 400 about the longitudinal axis O as illustrated by arrow 710. This is advantageous as any uneven heating loads due to the plasma 42 which are generated (for example due to convection of the gas in the container 400) can be made to have a equal effect around the circumference of the container 400. As a result large thermal gradients can be avoided. Additionally this embodiment makes use of the variation in density in the gas in the container 400. The hottest gas, namely that in the plasma 42, will be least dense and other parts of the gas not formed in the plasma 42 will be more dense. The hottest parts of the gas not in the plasma 42 will have a lower density than the cooler parts. As a result of centrifugal forces, the cold and more dense gas will be pushed to the outside of the container 400 and the lighter gas and plasma 42 will concentrate in the center along the longitudinal axis O. This has the effect of decreasing the plasma 42 size and therefore has a positive effect on the plasma 42 intensity. This is because the size of the plasma 42 will be reduced and it will act more like a point source thereby increasing the overall efficiency of the radiation source. Additionally, any convection in the gas in the container 400 is not as strong thereby resulting in warmer plasma and lower thermal gradients within the container 400. Finally, the plasma 42 will advantageously be kept hotter due to the presence of the hottest gas being next to the plasma 42. A suitable speed for rotation may be more than 100 revolutions per minute, for example above 500 revolutions per minute, perhaps as much as 1000 revolutions per minute or more.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. As already mentioned, the invention may be applied in industrial processing applications quite separate from lithography. Examples might be in production of optical components, automotive manufacture, construction—any number of applications where object data exists in the form of measurements made with a certain spatial distribution over the product. As in the example of lithography, the set of measurements that is subjected to multi-variate analysis can be measurements made for different product units, and/or different instances of measuring the same product units. Although specific reference may have been made above to the use of embodiments of the invention in the context of optical lithography, it will be appreciated that the invention may be used in other types of lithography, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams. As mentioned above, the term radiation in the context of the driving system may also encompass microwave radiation.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiment, but should be defined only in accordance with the following claims and their equivalents.

The invention claimed is:

1. A radiation source comprising:
a container arranged to be pressurized with a gaseous medium in which plasma which emits plasma emitted radiation is generated following excitation of the gaseous medium by a driving radiation, said container comprising:
an inlet radiation transmitting element operable to transmit said driving radiation from outside said container to inside said container, and
an outlet radiation transmitting element operable to transmit at least some of said plasma emitted radiation from inside said container to outside said container as output radiation;
wherein the center of the plasma is between three to six times as far from said outlet radiation transmitting element and/or said inlet radiation transmitting element as from the nearest wall of the container, and
wherein said container has a non-spherical, elongated shape and an axis of symmetry along which the output radiation is transmitted, and the inlet radiation transmitting element and the outlet radiation transmitting element are perpendicular to the axis of symmetry.

2. The radiation source of claim 1, wherein the container defines:
an inlet volume through which said driving radiation passes,
an outlet volume through which plasma emitted radiation passes, and
a plasma surrounding volume surrounding said plasma,
wherein an average cross sectional area of the inlet volume and/or outlet volume in a plane perpendicular to an optical axis of the radiation source is greater than an average cross-sectional area of the plasma surrounding volume in a plane perpendicular to the optical axis of the radiation source.

3. The radiation source of claim 1, wherein said container is operable substantially to remove radiation with a wavelength of 10-400 nm from said plasma emitted radiation before said plasma emitted radiation exits said container as output radiation.

4. The radiation source of claim 1, wherein both said inlet and outlet radiation transmitting elements comprise a plain parallel plate.

5. The radiation source of claim 1, wherein said container has side walls that comprise a material more able to withstand plasma emitted radiation than the input and output radiation transmitting elements.

6. The radiation source of claim 1, wherein said container has side walls that comprise a material more able to withstand plasma emitted radiation than the input and output radiation transmitting elements.

* * * * *